US00PP12129P2

(12) United States Plant Patent
Zary

(10) Patent No.: US PP12,129 P2
(45) Date of Patent: Oct. 9, 2001

(54) FLORIBUNDA ROSE PLANT NAMED 'JACTORSE'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/405,423

(22) Filed: Sep. 22, 1999

(51) Int. Cl.[7] ..... A01H 5/00
(52) U.S. Cl. ..... Plt./142
(58) Field of Search ..... Plt./141, 142, 143, Plt./149, 150, 130, 131, 132

*Primary Examiner*—Howard J. Locker
(74) *Attorney, Agent, or Firm*—Klarquist Sparkman Campbell Leigh & Whinston, LLP

(57) ABSTRACT

Floribunda rose plant having bright, deep pink or light red flowers with a light pink reverse presented in large, open clusters; vigorous, upright growth habit; and dark green, very glossy foliage having excellent disease resistance.

1 Drawing Sheet

The present invention relates to a new and distinct variety of rose plant of the floribunda class which was originated by me by crossing the variety 'JACient' (U.S. Plant Pat. No. 6,725), with an unnamed red floribunda (not patented).

The primary objective of this breeding was to produce a new rose variety having the excellent health, the glossy, dark green foliage, and the large open clusters of the female parent, combined with the bright red flower color of the unnamed seedling floribunda male parent. The objective was substantially achieved, along with other desirable improvements, as evidenced by the following unique combination of characteristics that are outstanding in the new variety and that distinguish it from its parents, as well as from all other varieties of which I am aware:

1. Bright, deep pink or light red flower with a light pink reverse;
2. Flowers presented in large, open clusters;
3. Vigorous, upright growth habit;
4. Dark green, very glossy foliage; and
5. Excellent disease resistance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'JACient' (U.S. Plant Pat. No. 6,725).

*Pollen parent.*—Unnamed red floribunda (unnamed seedling×unnnamed seedling — not patented).

Classification:

*Botanical.*—*Rosa hybrida.*

*Commercial.*—Floribunda.

FLOWER

Observations made from specimens grown in a garden environment at Somis, Calif., March 1998 to August 1999.

Blooming habit: Continuous.

Bud:

*Size.*—One inch long when the petals start to unfurl.

*Form.*—The bud form is short; pointed ovoid.

*Color.*—When sepals first divide, bud color is Red Group 53D with some areas of Red Group 53A where the bud was exposed early to sunlight. When half blown, the upper sides of the petals are Red Group 45D with a distinctive Yellow Group 6D patch at the petal base; and the lower sides of the petals are Red Group 49C with a Yellow Group 4A patch at the petal base.

*Sepals.*—Color: Green Group 138B with, when exposed to bright sunlight, a light cast of Greyed-Purple Group 184D. Surface texture: Covered in fine hairs. There are three heavily appendaged sepals. There are two unappendaged sepals with hairy edges.

*Receptacle.*—Color: Yellow-Green Group 146B, except when exposed to bright sunlight; then it is Greyed-Purple Group 183B. Shape: Funnel. Size: Medium, about 7/16 inches×5/16 inches. Surface: Smooth.

*Peduncle.*—Length: Short, averaging about 1¾ inches. Surface: Smooth. Color: Yellow-Green Group 146B, except when exposed to bright sun; then it is a Greyed-Purple Group 183B. Strength: Stiff; erect.

Bloom:

*Size.*—Medium. Average open diameter is about 3½ inches.

*Borne.*—Several together in pyramidal clusters of three to nine blooms.

*Stems.*—Strength: Strong. Average length is about 12–16 inches.

*Form.*—When first open: High centered. Permanence: Flattens; outer petals curl back.

*Petalage.*—Number of petals under normal conditions: 25–30.

*Color.*—The upper sides of the petals are Red Group 45D with a distinctive Yellow Group 6D patch at the petal base. The reverse sides of the petals are Red Group 49C with a Yellow Group 4A patch at the petal base. The base of each petal has a small, 1/16"×1/16", Yellow Group 7A half moon at the point of attachment on the upper side. The lower side has a similar mark, but it is Yellow Group 7C. The major color on the upper side is Red Group 45D.

*Variegations.*—There are on some petals, small streaks of Yellow Group 6D.

*Discoloration.*—The general tonality at the end of the first day: No change. At the end of the third day: No change. At day five or six, the upper petals change to Red-Purple Group 57B, and on day six or seven to Red-Purple Group 57C. By day seven, the petals drop.

*Fragrance.*—Slight; apple.

Petals:

*Texture.*—Thick.

*Shape.*—Deltoid.

*Form.*—Tips slightly recurved; edges slightly quilled.

*Arrangement.*—Imbricated. Petaloids in the center: None.

*Persistence.*—Petals drop off cleanly before drying.

*Lastingness.*—On the plant: Fair (about six days). As a cut flower: Fair (about seven to eight days).

Reproductive parts:

*Anthers.*—Size: Medium. Quantity: Many. Color: Yellow-Orange Group 22C. Arrangement: Regular around styles.

*Filaments.*—Color: Yellow-Orange Group 14A.

*Pollen.*—Present.

*Styles.*—Color: Green-White Group 157B.

*Stigmas.*—Color: Yellow-White Group 158A.

Plant:

*Form.*—Bush.

*Growth.*—Vigorous; upright; branching. At maturity, height is 40–44 inches, width is 32–36 inches.

Foliage: Number of leaflets on normal mid-stem leaves: five.

*Size.*—Large (about 5 to 5½ inches long×4 to 4½ inches wide).

*Quantity.*—Abundant.

*Color.*—New foliage: Upper and lower surfaces: Greyed-Purple Group 183A. Old foliage: Upper surface: Green Group 139A. Lower surface: Green Group 137A.

Leaflets:

*Shape.*—Pointed oval.

*Texture.*—Leathery; glossy.

*Edge.*—Serrated.

*Serration.*—Single; small.

*Petiole rachis.*—Color: Upper: Greyed-Purple Group 183B, turning to Green Group 137D with age. The lower surface is Yellow-Green Group 148B.

*Petiole underside.*—Smooth.

*Stipules.*—Long (about ¾ inches); serrated; bearded.

*Disease resistance.*—Resistant to mildew and rust, and tolerant of blackspot under normal growing conditions.

Wood:

*New wood.*—Color: Greyed-Purple Group 183A. Bark: Smooth.

*Old wood.*—Color: Green-Group 137A with a cast of Greyed-Purple Group 183B until the wood is fully mature. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 183D.

*Color when mature.*—Greyed-Red Group 181C.

Small prickles:

*Quantity.*—On main stalks: None. On laterals: None.

I claim:

1. A new and distinct variety of rose plant of the floribunda class, substantially as herein shown and described, characterized particularly by its bright, deep pink or light red flowers with a light pink reverse presented in large, open clusters; vigorous, upright growth habit; and dark green, very glossy foliage having excellent disease resistance.

* * * * *

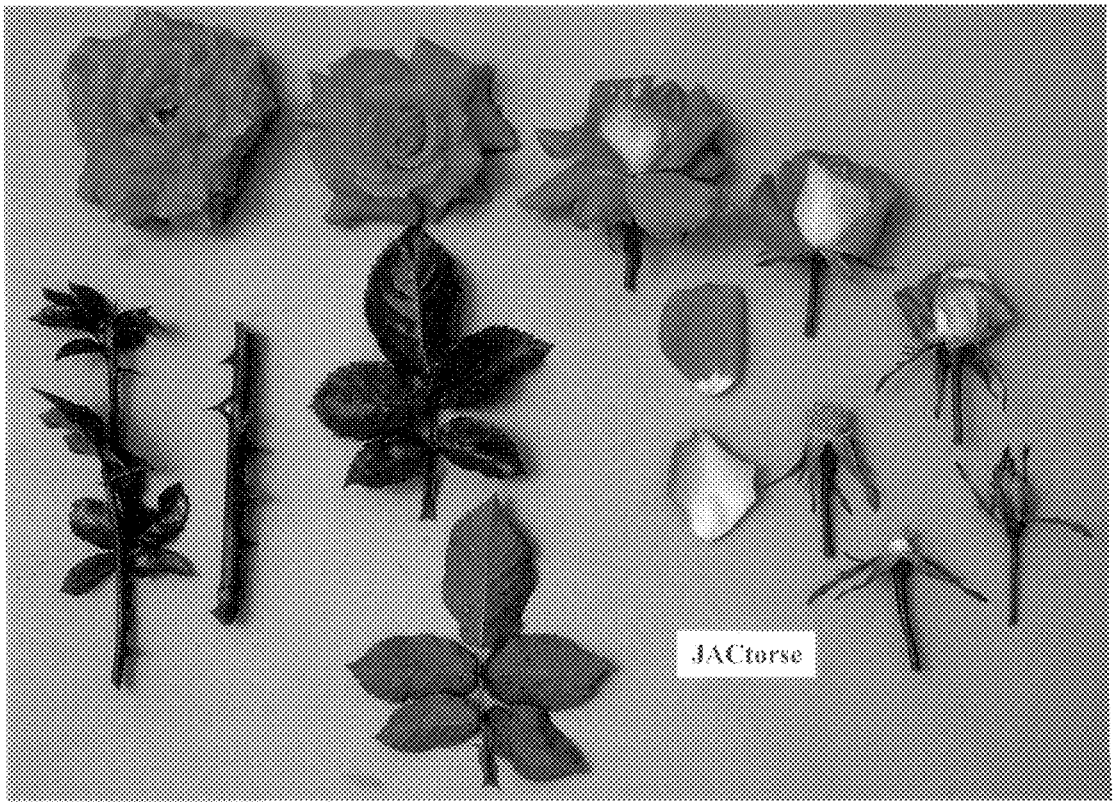
JACtorse